(12) United States Patent
Shertukde et al.

(10) Patent No.: US 6,178,386 B1
(45) Date of Patent: Jan. 23, 2001

(54) METHOD AND APPARATUS FOR FAULT DETECTION

(75) Inventors: Hemchandra M. Shertukde, Simsbury; Hisham Alnajjar, New Britain, both of CT (US)

(73) Assignee: The University of Hartford, West Hartford, CT (US)

(*) Notice: Under 35 U.S.C. 154(b), the term of this patent shall be extended for 0 days.

(21) Appl. No.: 09/134,404

(22) Filed: Aug. 14, 1998

(51) Int. Cl.[7] ............................................ G01N 29/12
(52) U.S. Cl. ................................. 702/56; 336/145
(58) Field of Search .......................... 336/145; 702/56, 702/58; 324/520, 527, 528, 544

(56) References Cited

PUBLICATIONS

R.H. Shertukde, H.M. Shertukde "Manufacture of Fault Diagnostic Device for Electrical Power Transformers $(FD^2-EPT)$".

Hemchandra M. Shertukde, Hisham Alnajjar, Uday Prabhune "Fault Detection Device For Electrical Power Transformers Using Noval DSP Scheme".

*Primary Examiner*—Patrick Assouad
*Assistant Examiner*—Edward Raymond
(74) *Attorney, Agent, or Firm*—Pepe & Hazard LLP

(57) ABSTRACT

A partial discharge fault in a transformer tank is determined by sensing supersonic vibrations at a multiplicity of points about the tanks and establishing a threshold amplitude and a frequency range for pulse vibrations to be evaluated. The signals from the multiplicity of points are multiplexed, synchronized and localized and then processed in a series of steps. After the existence of triggering pulse vibrations exceeding an established threshold amplitude and within an established frequency and range is initially determined, a wavelet transform is conducted on the multiplexed signals two at a time with one signal being the signal from the first sensor found to provide a signal above the threshold amplitude. The wavelet transform provides both frequency and time domain. A scaling factor and translation parameters associated with the frequency of the vibrations are applied to obtain estimates of the time delays for the triggering pulse vibrations detected at the multiplicity of points, and the estimates of the transformed and scaled signals are then evaluated to determine the position of the partial discharge fault generating the triggering pulse vibrations.

10 Claims, 19 Drawing Sheets

SYSTEM SOFTWARE DETAILS

- K_OpenDriver("DAS4100","DAS4100.CFG",&hDrv4100)
  SPECIFIES THE DATA ACQUISITION BOARD, THE CONFIGURATION FILE AND THE HANDLE ASSOCIATED.

- K_GetDevHandle(hDrv4100,0,&hDev4100)
  SPECIFIES THE DRIVER HANDLE AND THE CORRESPONDING DEVICE HANDLE

- K_GetADFrame(hDev4100, &hAD)
  SPECIFIES DEVICE HANDLE AND THE CORRESPONDING FRAME HANDLE

- K_SetBuf(hAD, Buffer1, TotalSamples)
  SPECIFIES THE FRAME HANDLER THE DATA BUFFER AND THE TOTAL NUMBER OF SAMPLES

- K_SetStartStopChn(hAD,0,1)
  SPECIFIES THE START CHANNEL AS '0' AND STOP CHANNEL AS '1'

- K_SetChnGAry(hAD, &ChanGainArray)
  SETS THE CHANNEL GAINS ACCORDING TO THE GAINS IN THE CHANNEL GAIN ARRAY

- K_SetClk(hAD, 1)
  SETS THE PACER CLOCK SOURCE AS AN EXTERNAL CLOCK

- K_SetClkRate(hAD, 256)
  SETS THE PACER CLOCK TO ITS ORIGINAL RATE (FULL - 'DIVISOR = 1')

- K_SetTrig(hAD, 0)
  SETS THE TRIGGER SOURCE AS AN INTERNAL ONE

- K_IntStart(hAD)
  STARTS THE INTERRUPT MODE DATA ACQUISITION

- K_IntStatus(hAD, &Status, &Index)
  CHECKS THE STATUS OF DATA ACQUISITION AND UPDATES THE STATUS VARIABLE (SHORT) 'STATUS' AND THE COUNT INDEX VARIABLE ( DOUBLE WORD) 'INDEX'

- K_CloseDriver(hDrv4100)
  CLOSES THE DRIVER AND MAKES THE HANDLE AVAILABLE FOR NEXT DATA ACQUISITION

*FIG. 8*

METHOD AND APPARATUS FOR FAULT DETECTION

BACKGROUND OF THE INVENTION

The present invention relates to preventing transformer breakdowns and, more particularly, to a method for determining the early location of faults in transformers to enable repair before their catastrophic failure.

Power utilities utilize large numbers of transformers in their power distribution system, and the failure of such transformers can cause power outages or substantial power fluctuation.

Frequently, transformer failure occurs as the result of breakdown in the insulation in the transformer tanks. A partial discharge (PD) occurs due to the breakdown of a small part of the transformer insulation, generally caused by the inclusion of moisture or the presence of a cavity. This activity results in an instantaneous shunting of a small partial capacitance which burgeons into catastrophic failure of the entire insulation. It has been recognized that incipient failures are frequently reflected by partial discharge pulses (PD) generated at the areas of insulation breakdown, and that, if such locations can be accurately identified through partial discharge signals, repairs can be made expeditiously and relatively economically to prevent catastrophic failure.

When a PD takes place within the confines of a transformer, it emits mechanical stress waves with subsequent resonance in the frequency range of 50–350 kHz. Sensors which are placed on the outside surface of the transformer tank, can detect the waves which may have propagated from the PD source through the internal core, winding, insulation materials and oil to the transformer tank wall. The waves detected by a piezoelectric sensor on the transformer tank wall have a waveform.

This signal often manifests a bursty nature and is a non-stationary random process. It also represents an admissible kernel representation for using wavelet transform (WT) in appropriate signal processing algorithms. High time-bandwidth, spread spectrum signals that experience time-scaling are difficult to decompose with narrowband analysis, such as Fourier transform, due to its sinusoidal kernel, which approximates the scaling effect with a Doppler shift. However, the WT, utilizes a more general analysis kernel, or mother wavelet.

In "*Electrical Power Transformers*" by R. H. Shertukde et al, Proceedings ICSPAT, Boston, October 1996, pages 1229–1986, there are described apparatus and methods for achieving online monitoring of transformers to identify incipient faults, and there is proposed a technique for utilizing wavelet transform techniques for increasing the accuracy of locating the incipient fault. Although such technology has been proposed as providing a more reliable measurement, the costs associated with the electronics to achieve the desired processing of a large number of signals from the multiplicity of ultrasonic sensors needed has represented a substantial impediment to widespread usage as has been the need to process the signals effectively.

It is an object of the present invention to provide a novel method for detecting and determining the position of partial discharge signals in a transformer tank.

It is also an object to provide such a method which can be produced readily, reliably and relatively economically.

Another object is to provide novel apparatus to conduct the detection and position determination.

A further object is to provide such apparatus which may be fabricated from readily available components at a reasonable cost to enable its widespread use.

SUMMARY OF THE INVENTION

It has now been found that the foregoing and related objects may be readily attained in a method for determining the position of a partial discharge fault in a transformer tank in which supersonic sensors are secured on a transformer tank at a multiplicity of points spaced about the periphery thereof. A threshold amplitude and a frequency range for pulse vibrations to be evaluated are established, and supersonic vibrations are sensed at the multiplicity of points. The signals from the sensors are transmitted to an interface at which the signals from the multiplicity of points are multiplexed, synchronized and localized, following which they are transmitted to a processor.

The multiplexed signals are then processed by steps including:

1. Initially, there is a determination of the existence of triggering pulse vibrations exceeding the established threshold amplitude and within the established frequency range.
2. A wavelet transform is then conducted on the multiplexed signals from the sensors at the multiplicity of points, two at a time with one signal being the signal from the first sensor found to provide a signal above the threshold amplitude. This wavelet transform provides both frequency and time domain.
3. A scaling factor and translation parameters associated with the frequency of the vibrations are applied to obtain estimates of the time delays for the triggering pulse vibrations detected at the multiplicity of points.
4. These time estimates from the transformed and scaled signals are then evaluated to determine the position of the partial discharge fault which generated the triggering pulse vibrations.

The processing step initially generates a triggering signal to the interface upon sensing a signal of greater amplitude than the predetermined value and initiates the further processing steps to determine the position of a fault.

In the processing step, the multiplexed signal are passed into a data acquisition board which samples signals in several channels at a predetermined minimum sampling frequency per channel which is determined by the Nyquist Criterion. A clock circuit is employed to time the signals being processed in the multiplexing and processing steps.

BRIEF DESCRIPTION OF THE DRAWINGS

FIG. 8 is a listing of the factors in the initialization;

DETAILED DESCRIPTION OF THE PREFERRED EMBODIMENT

In accordance with the method of the present invention, partial discharge faults can be readily monitored and located by positioning a multiplicity of supersonic sensors at spaced points about the housing of the transformer, detecting supersonic vibrations emanating from various locations in the transformer and processing the signals represented by vibrations which exceed a threshold amplitude and are within a specified frequency range by a series of steps which will be described in detail hereinafter. However, to process the multiplicity of signals efficiently, the signals from the sensors are initially passed through an interface which multiplexes, synchronizes and localizes them.

To facilitate understanding of the present invention, there are basic factors to be considered.

Figure 1:
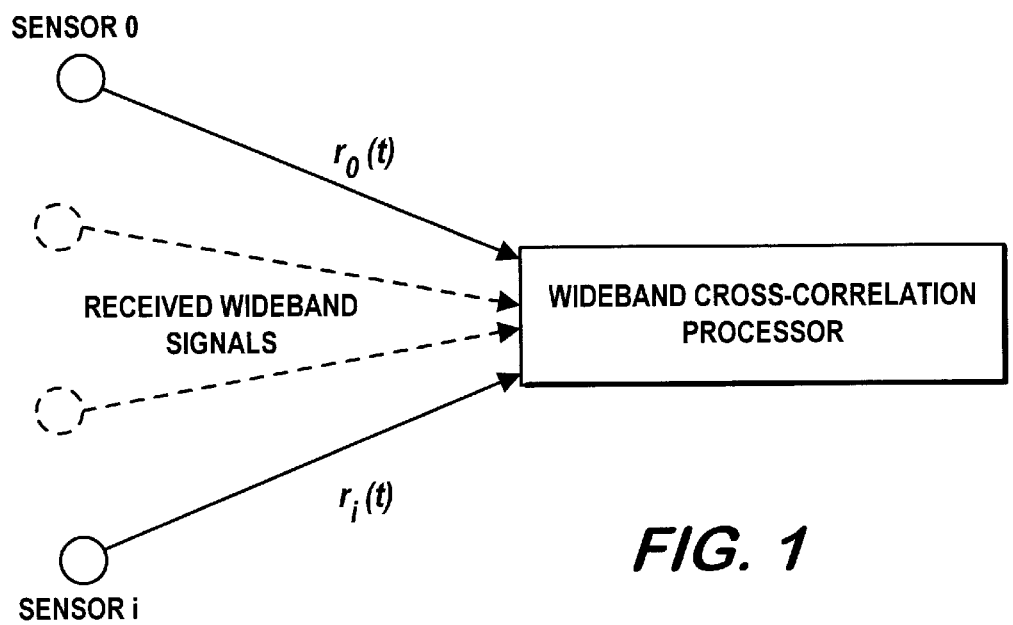
FIG. 1 is a diagrammatic representation of processing a pair of signals.

In a passive system of the type shown in FIG. 1, no transmitted signal exists and only two (or more) received signals from the sensors are available. If one of the received signals is chosen as the reference signal (mother wavelet), then it can be scaled and translated and compared to or correlated with the other received signals. This correlation of received signals with scaled and delayed versions of reference signals, forms a wide-band cross ambiguity function, and the peaks indicate the relative time-scale and time-delay of the multipaths. Estimation of these Relative Normalized Time Difference Of Arrivals (RNTDOAS) can then be used effectively to project the geometric location of the PD source (assumed to be a point source).

The PD signal is defined as $\chi(t)$. The attenuated, scaled and delayed versions of the PD signal corrupted by noise will be received by the sensors which are located on the external surface of the transformer tank. This suggests the following model for the received signal at sensor i.

$$r_i(t) = \frac{a_i}{\sqrt{s_i}} x\left[t - \frac{\tau_i}{s_i}\right] + n_i(t) \quad \text{Where } i = 0, 1..., \text{ and } n - 1 \quad (1)$$
$$= x_i(t) + n_i(t)$$

The noise $n_i(t)$ is modeled as independent, identically distributed Gaussian value with mean zero and variance $\sigma_i^2$. It is also uncorrelated with the received signal $\chi_i(t)$. If the signal received at sensor 0 is considered to be the mother wavelet and $W_{r_0}r_i(s_1\tau)$ is considered to be the wavelet transform of signal $r_i(t)$ with respect to $r_0(t)$, the continuous wavelet transform computes the inner product of the function $r_i(t)$ with the scaled and delayed versions of the mother wavelet, $r_0 t$), as follows:

$$_{r_0}r_i(s, \tau) = \frac{1}{\sqrt{s}} \int r_i(t) r_0\left[\frac{t - \tau}{s}\right] dt \quad (2)$$

In order to allow reconstruction of $r_i(t)$ from its wavelet transform with $r_0(t)$, the mother wavelet $r_0(t)$ must satisfy the admissibility conditions of equations 1, 2, 3 & 6.

$$C_{r_0} = \int \frac{|R_0(\omega)|^2}{|\omega|} d\omega < \infty \quad (3)$$

Therefore, any real-time signal received in a system with finite duration and zero average value qualifies as a mother wavelet. Using the scale/delay property of WT yields $$W_{x_0}x_i(s, \tau) = \frac{a_0 a_i}{\sqrt{s_0}} s_i W\left[s\frac{s_0}{s_i}, \frac{\tau + s\tau_0 - \tau_i}{s_1}\right] \quad (4)$$

Since $W_{x\chi}$ will have a maximum value at $(s,\tau)=1,0)$, this equation will have a peak when $$s = \frac{s_i}{s_0} \text{ and } \tau = \tau_i - \frac{s_i}{s_0}\tau_0 \quad (5)$$

where $\tau$ refers to the RNTDOA with respect to the reference time domain of the PD source. If the reference time domain is changed to the time that the data is acquired, new equations can be developed.

Figure 2:
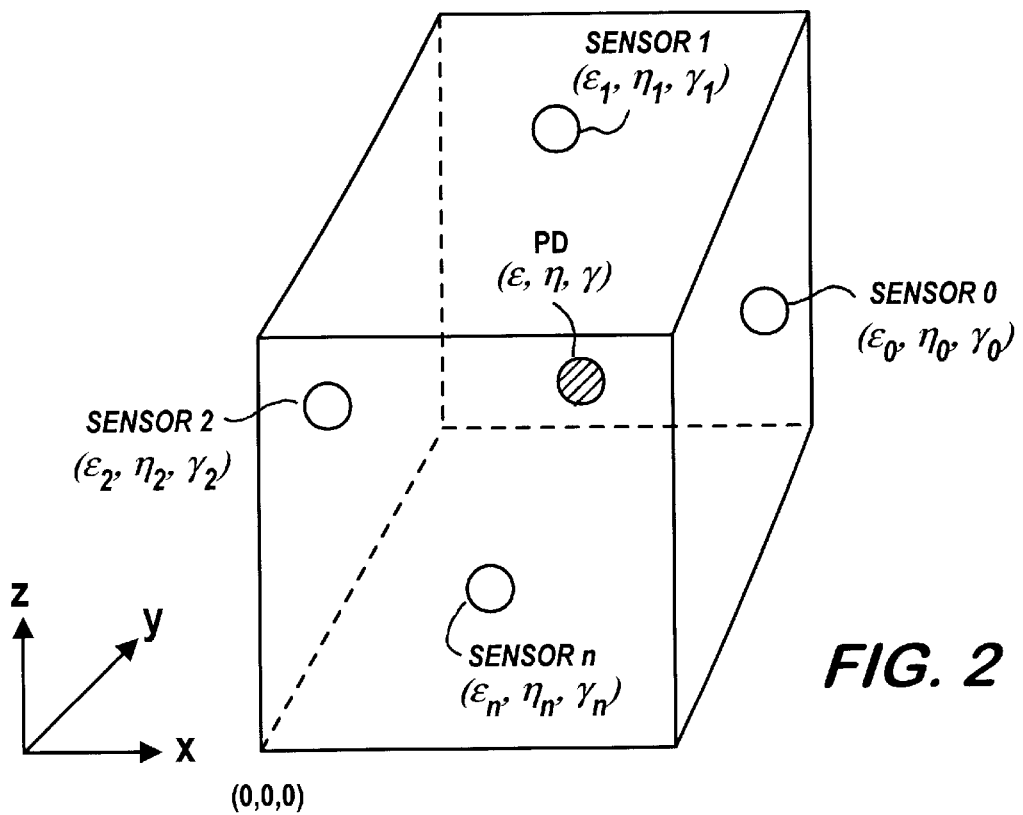
FIG. 2 is a diagrammatic illustration of a multiplicity of sensors disposed about the periphery of a transformer housing.

To illustrate the manner in which the PD source location can be determined, these are illustrated in FIG. 2 a transformer, a PD source and a multiplicity sensor locations. Assume (n+1) as the number of sensors located on the transformer tank, and the $i^{th}$ sensor location be denoted as $(\epsilon_i, \eta_i, \gamma_i)$ with respect to the origin (0,0,0). When the various acoustic emission travel times (RNTDOAs) have been determined, it is necessary to convert them to distances. This requires that they be multiplied by the velocity of sound in their propagation paths. The signals in a transformer probably travel through several materials, each exhibiting a different velocity. It is not possible to estimate an average velocity because the proportion of the journey devoted to each material is not known. Fortunately, a significant portion of the trip is in transformer oil and this material has the lowest acoustic velocity of all the component materials. Therefore, its value may be conveniently used in the calculations. Considering only oil as the main medium in the transformer and neglecting the heterogeneous combination of core, insulation of copper in the travel path, (n+1) equations can be obtained as shown below.

If the speed of sound in oil is c feet/sec, then $$(\epsilon-\epsilon_i)^2+(\eta-\eta_i)^2+(\gamma-\gamma_i)^2=c^2\cdot\tau_i^2 \quad (6)$$

The location of the PD can then be estimated using Matlab's Symbolic Toolbox and $\tau_i$.

Figure 3:
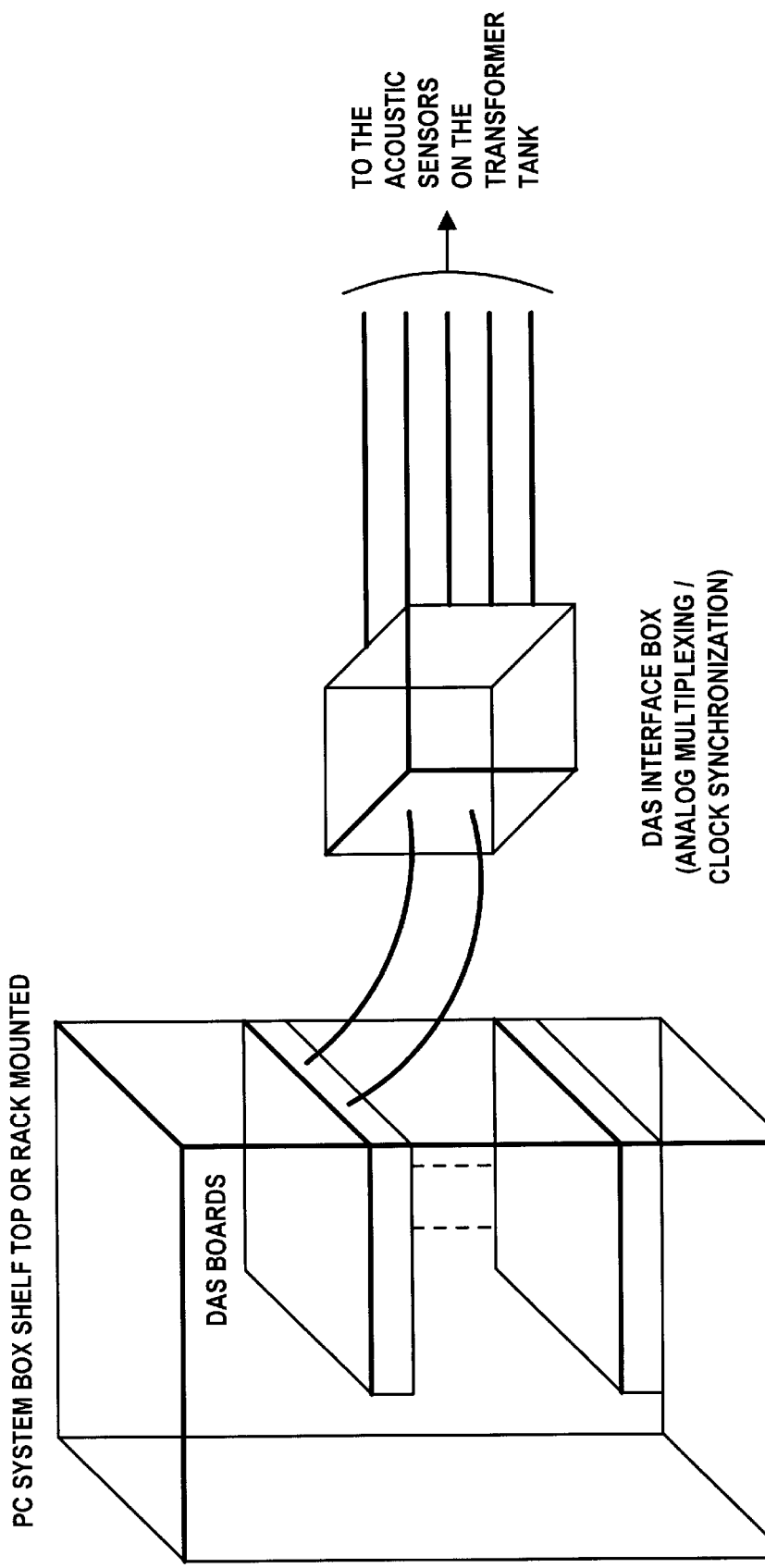
FIG. 3 is diagrammatic view of an installation embodying the present invention.

Thus, the method for processing the signals requires only a combination of readily available electronic components including the supersonic sensors, an interface board to receive and initially process the multiplicity of signals into synchronized, multiplexed and localized signals, a multiplicity of data acquisition boards (DAS Boards) to process the signals from the interface board, and a personal computer in which the DAS boards are installed. This assembly is diagrammatically illustrated in FIG. 3.

The acoustic sensors used are supersonic sensors and are placed on the walls of the transformer tank with magnetic hold-down devices. These acoustic sensors have built-in integrated preamplifiers.

The data acquisition boards are conveniently those sold by Keithley Metrabyte under the series designation DAS-4100. The DAS Board by itself has capability of acquiring the data from two channels simultaneously at a sampling rate of 64 MHz. However, more than eight sensors will generally be required for the "fault diagnosis" of a single transformer, depending upon its physical size. As the requirement of the number of sensors for data acquisition increases, the cost of the system increases considerably due to the increase in the number of DAS Boards required to process the signals. To reduce the cost of the overall system, an external multiplexing interface board is employed, which can handle data from eight sensors and pass the multiplexed data to a single DAS Board. The multiplexing hardware is housed in a DAS Interface Box containing one or more DAS Interface Boards (DAS I/F Boards). The number required will be determined by the number of sensor since each processes up to eight channels.

Figure 4:
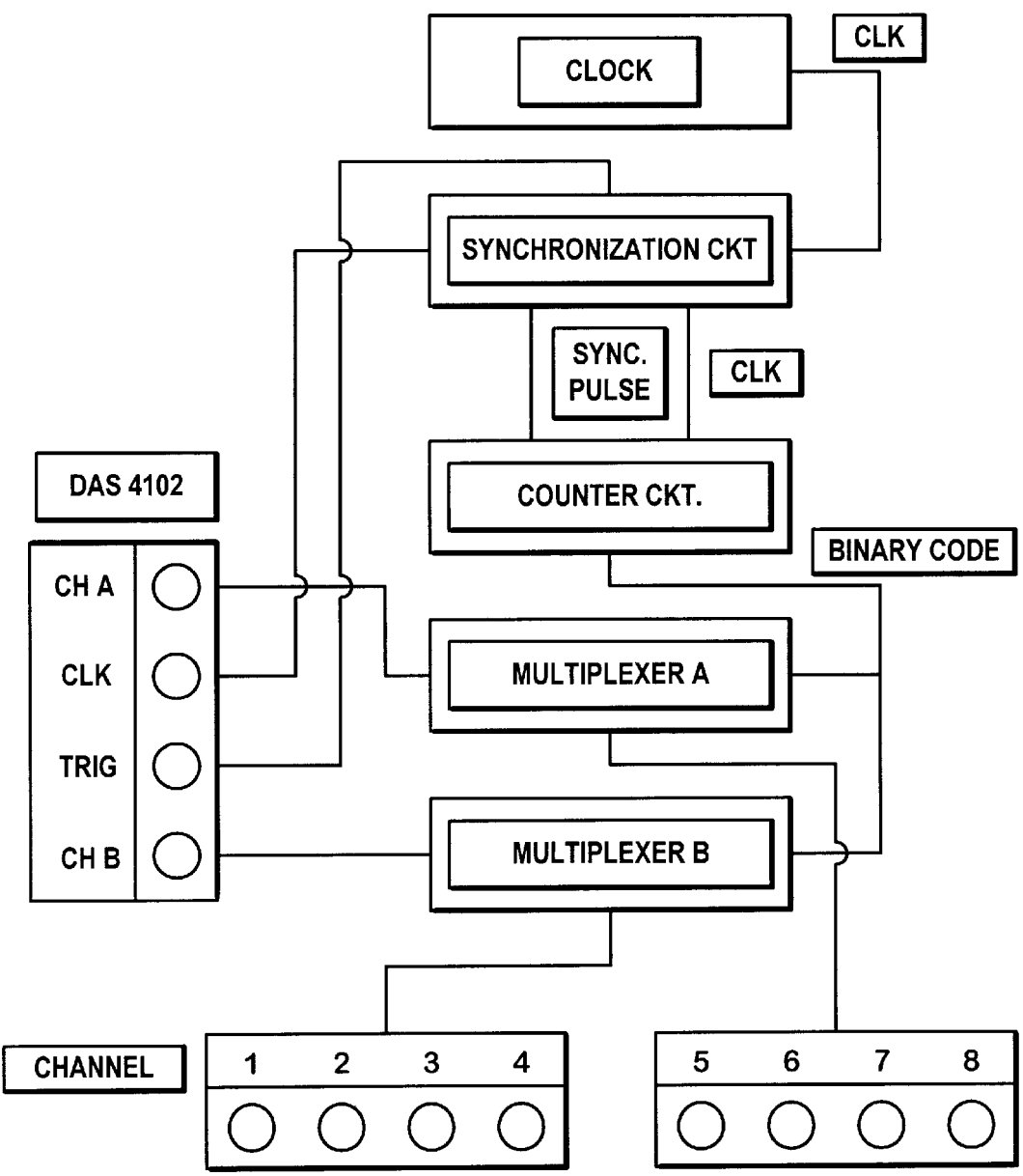
FIG. 4 is a functional block diagram of the DAS Interface Board.

The basic interface between the data acquisition board and the interface board is shown in FIG. 4 in which the channels represent the sensors and thereby localize the signals.

The important criteria which dictate the number of channels that can be accommodated by the two channels available on a DAS Board are:

a. the desired minimum sampling frequency per channel and b. the switching speeds of the associated hardware components.

The sampling frequency is decided by the Nyquist Criterion for the partial discharge signals. The partial discharge signals are generally in the frequency range of 50–350 KHz. The sampling therefore needs to be done at a sampling rate of 700 KHz or higher. The maximum switching speeds for the suitable analog multiplexers available, on the other hand, are of the order of 160 nanoseconds. The rest of the hardware circuit for DAS I/F Board is primarily digital, for which higher switching speeds are available and hence need not be considered for selecting the sampling frequency.

In order to implement the external multiplexing, two other factors are addressed in the DAS I/F Board, namely:

Clock Synchronization of data acquisition by the DAS Board with the external multiplexer, and Localization of the channels with respect to physical location of the sensors on transformer tank. The localizing functions of the DAS I/F Board labels a set of signals with digital identifiers representing the specific transducers.

Figure 5:
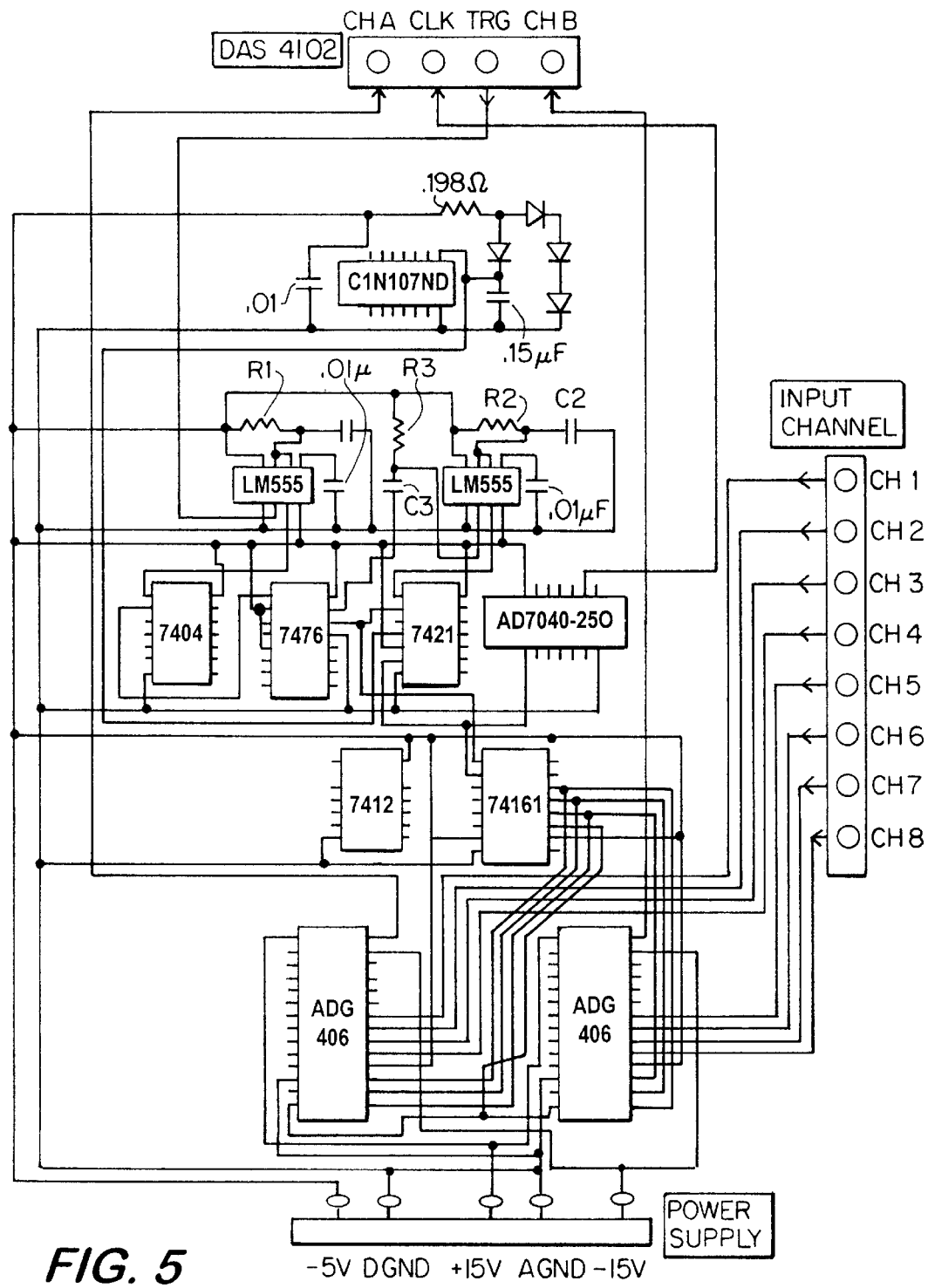
FIG. 5 is a circuit diagram of the DAS Interface Board.

The DAS Board by itself is completely unaware of the external multiplexing. As a result, the data acquired by the DAS Board is synchronized and localized to differentiate between the multiplicity of signals being processed. In order to ensure contemporaneous data availability and data acquisition, synchronization by the clock is required. The multiplexer circuit is the heart of the DAS I/F Board which is illustrated diagrammatically in FIG. 5. It basically consists of two analog multiplexers. All the channels exhibit break-before-make switching action to prevent momentary shorting when switching channels. Upon receiving a trigger signal from the DAS Board, a set of events occur and then the DAS I/F Board is ready for the actual data acquisition. It then awaits for a successor trigger from the DAS Board.

As seen in FIG. 4, the DAS I/F Board has the following:
1. Clock Circuit
2. Synchronization Circuit
3. Counter Circuit
4. Multiplexer Circuit The Clock Circuit provides external pacer clock at 4 MHz for the DAS Board and also for the Multiplexer Block. The synchronization Circuit also synchronizes the data availability from the Multiplexer Block and the data acquisition by the DAS Board. It also provides channel localization. The Counter Circuit provides addressing to the Multiplexer Circuit. The Multiplexer Circuit consists of two individual multiplexers and provides eight channel multiplexing.

Figure 6:
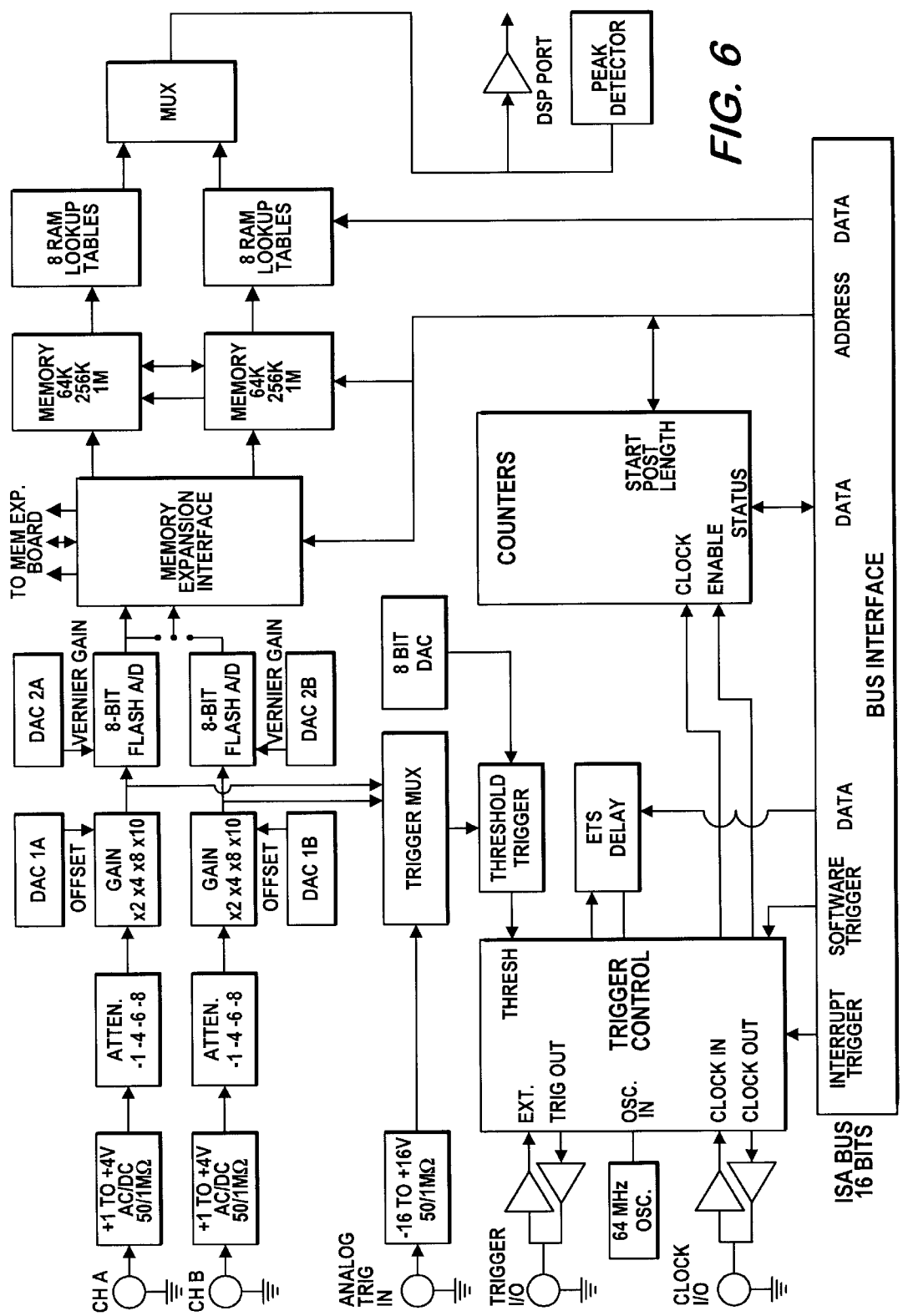
FIG. 6 is functional block diagram of the DAS Board.

FIG. 6 is a functional block diagram of a DAS-4100 Series board sold by Keithley Metrabyte which has proven highly effective as a processor in the practice of the present invention.

Figure 7:
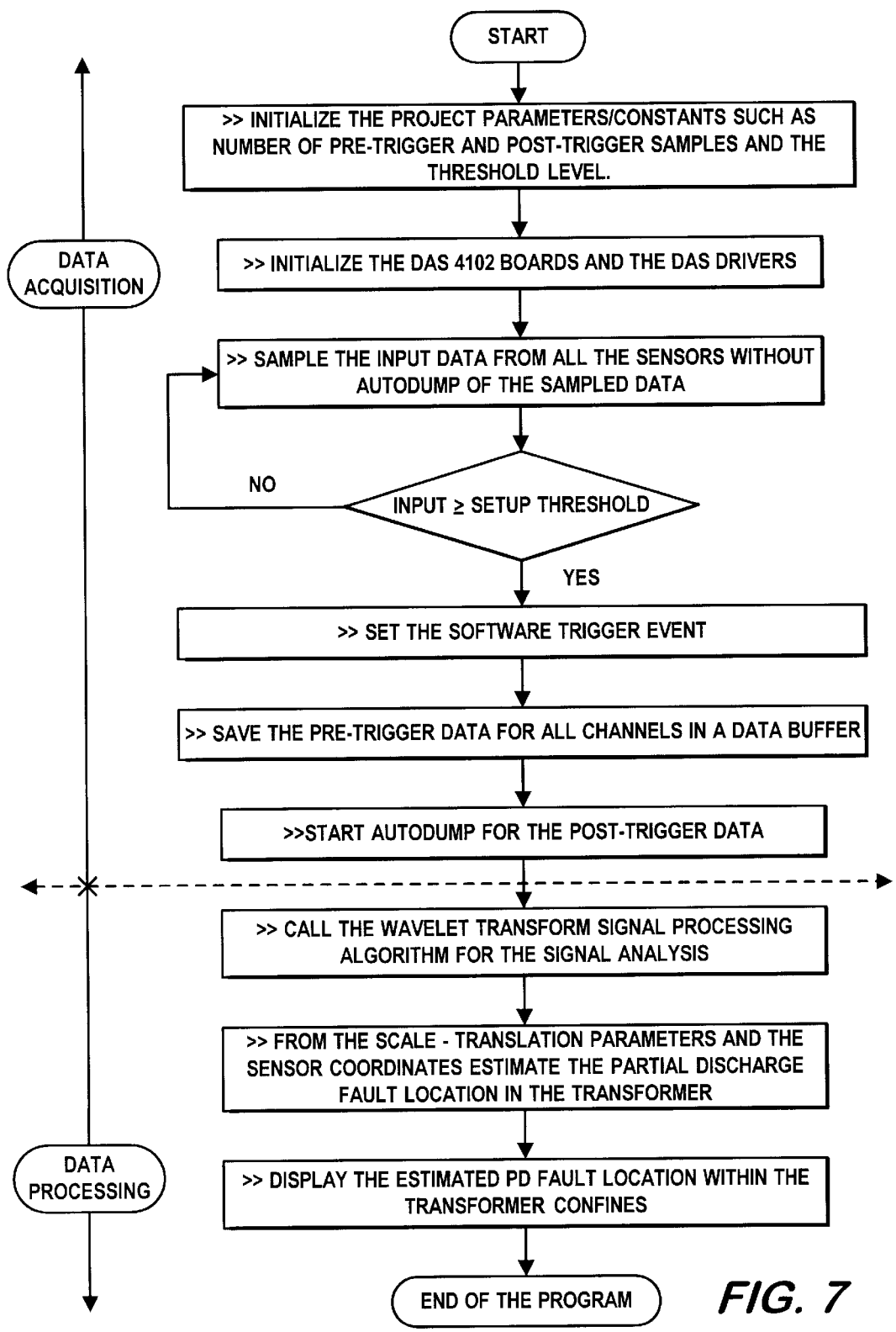
FIG. 7 is a flow chart functionally setting forth the several steps in the method of the present invention.
Figure 9A:
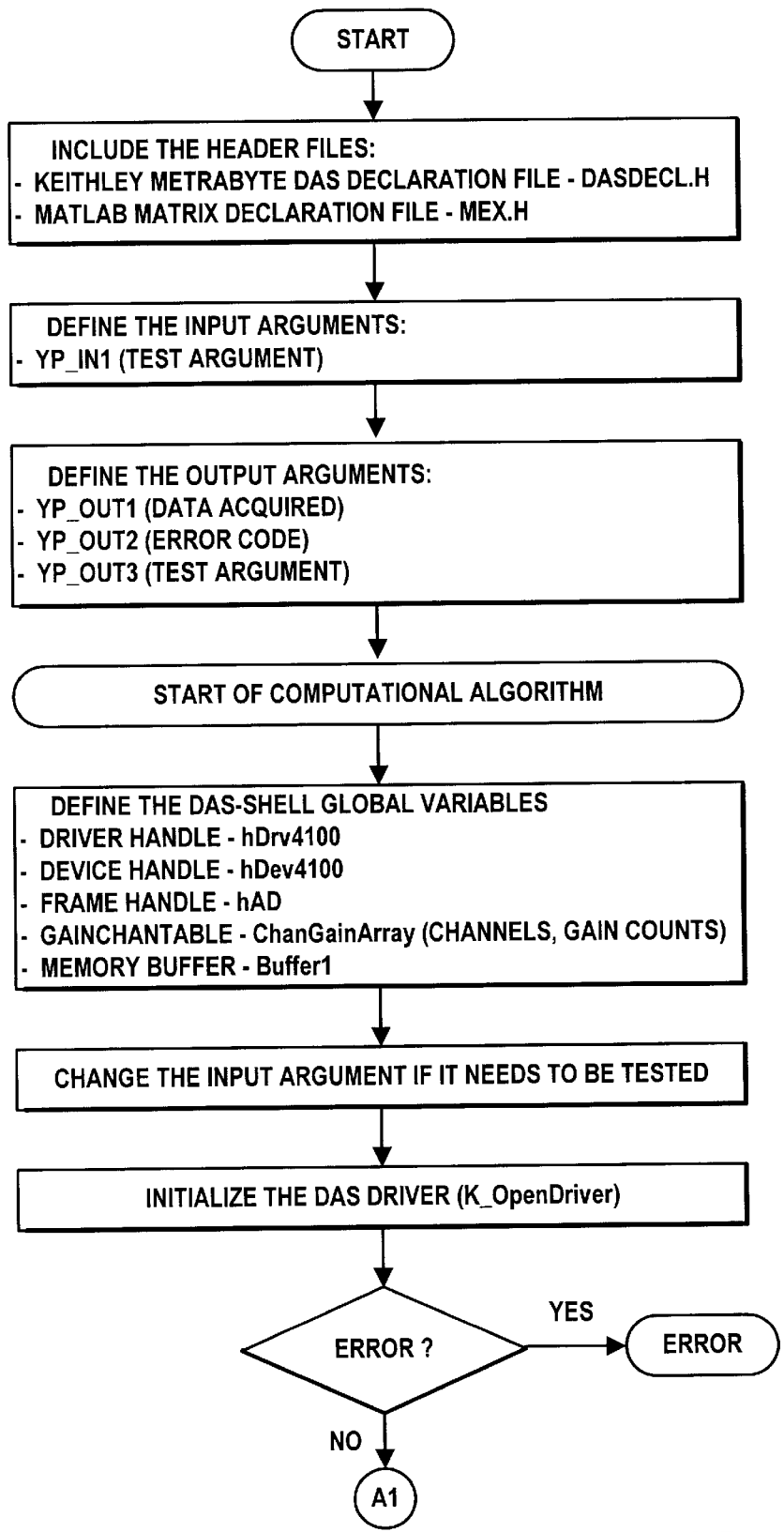
FIGS. 9a–9e comprise a flow chart of the software for the system initialization.
Figure 9B:
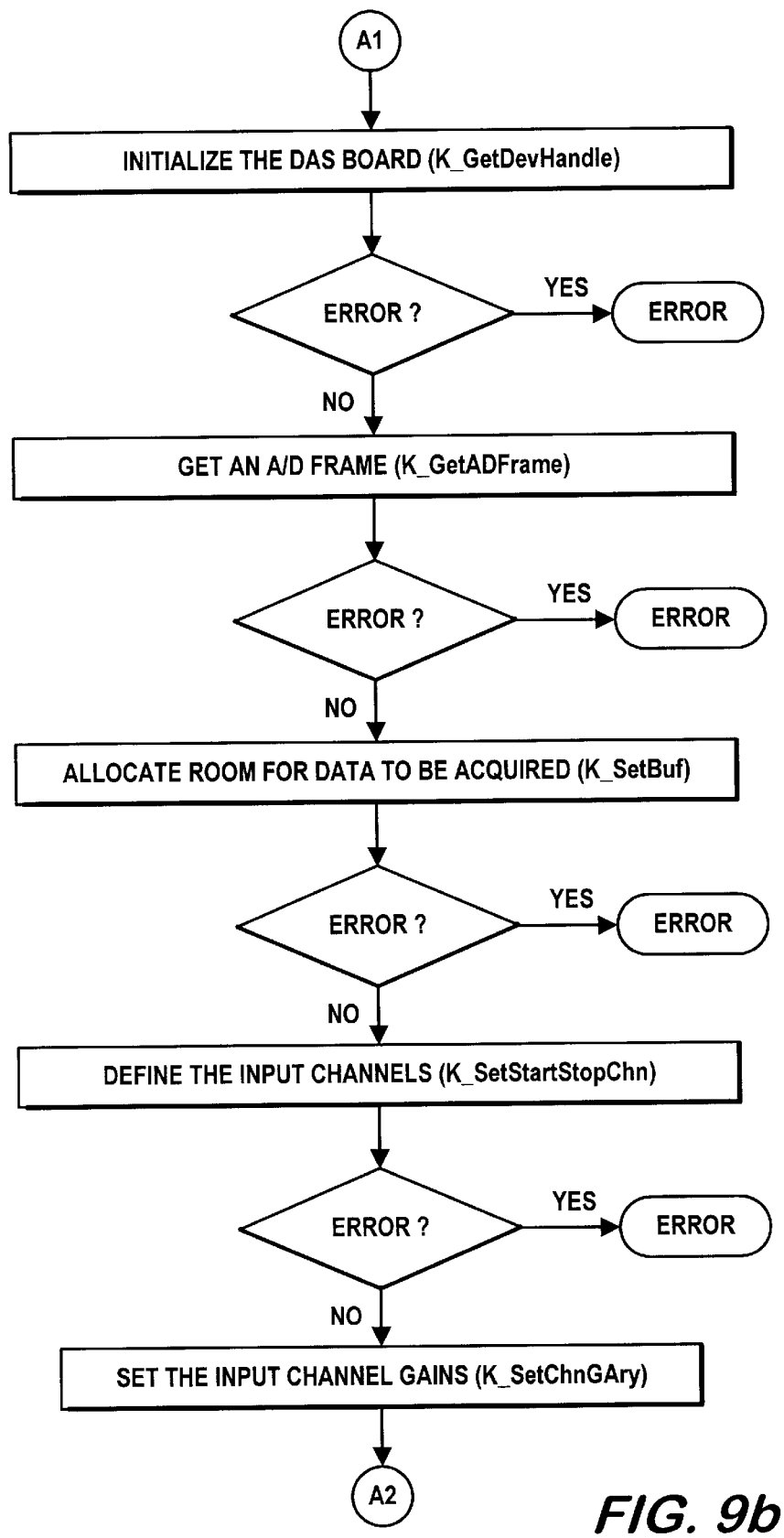
Figure 9C:
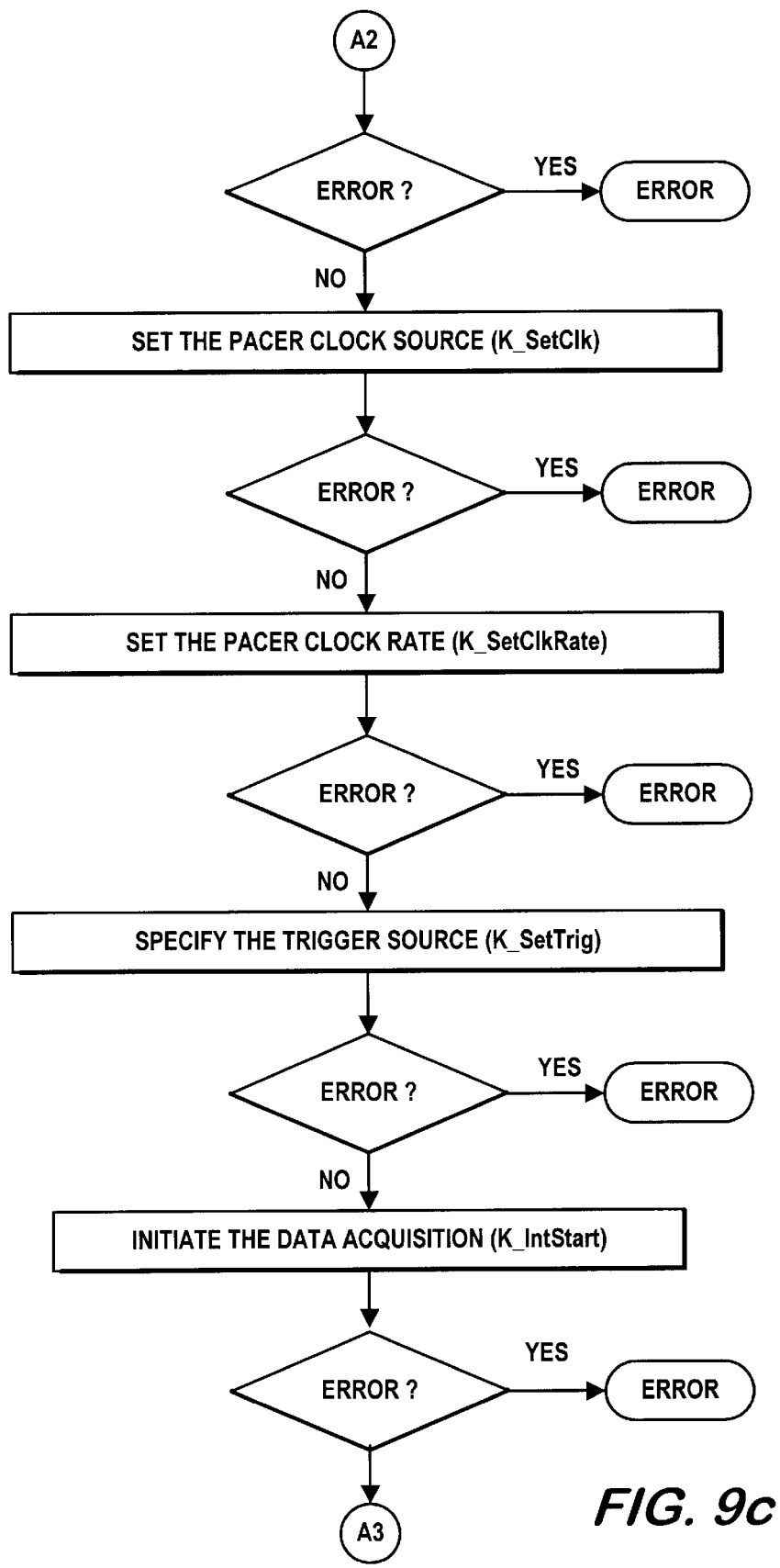
Figure 9D:
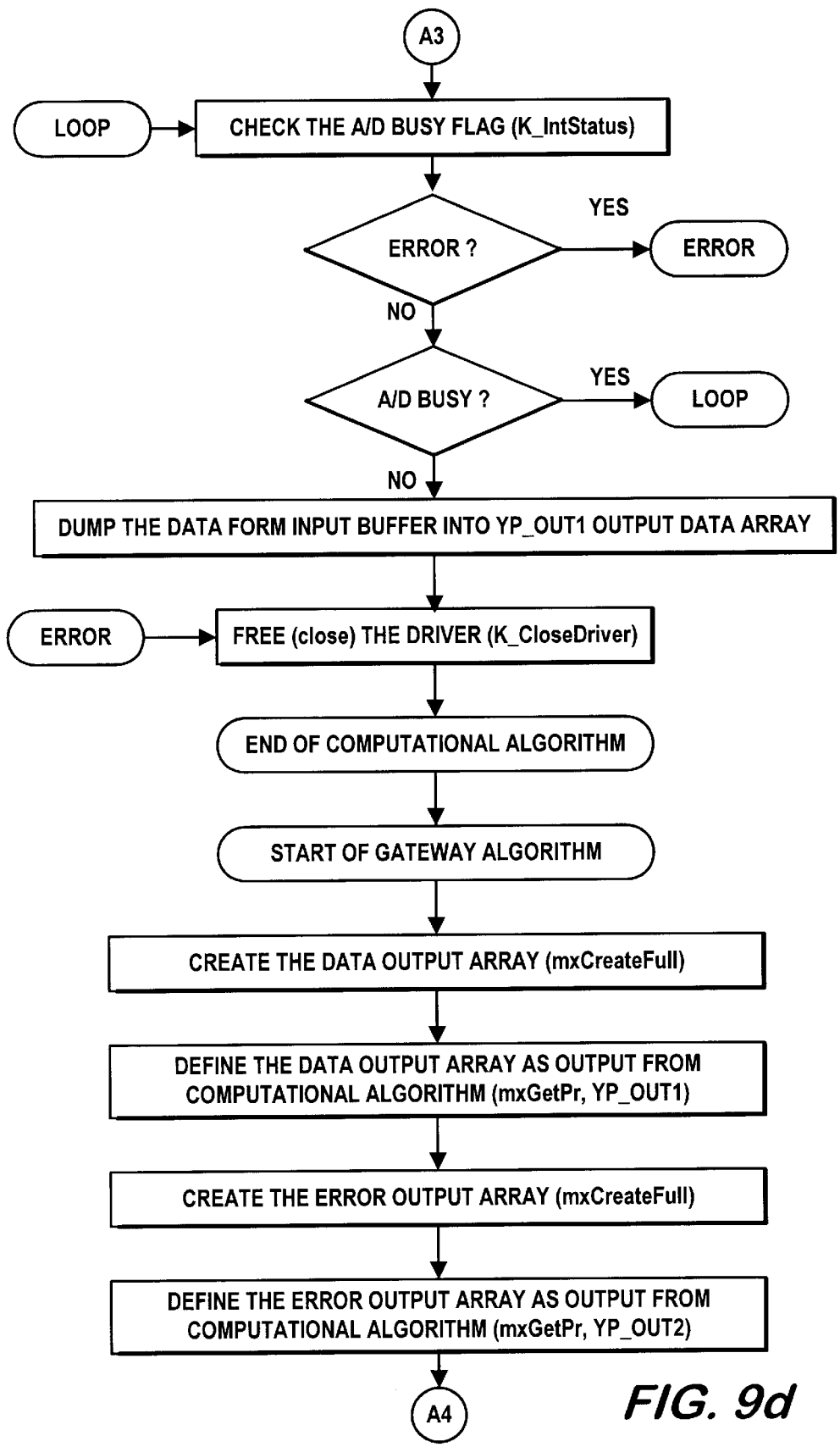
Figure 9E:
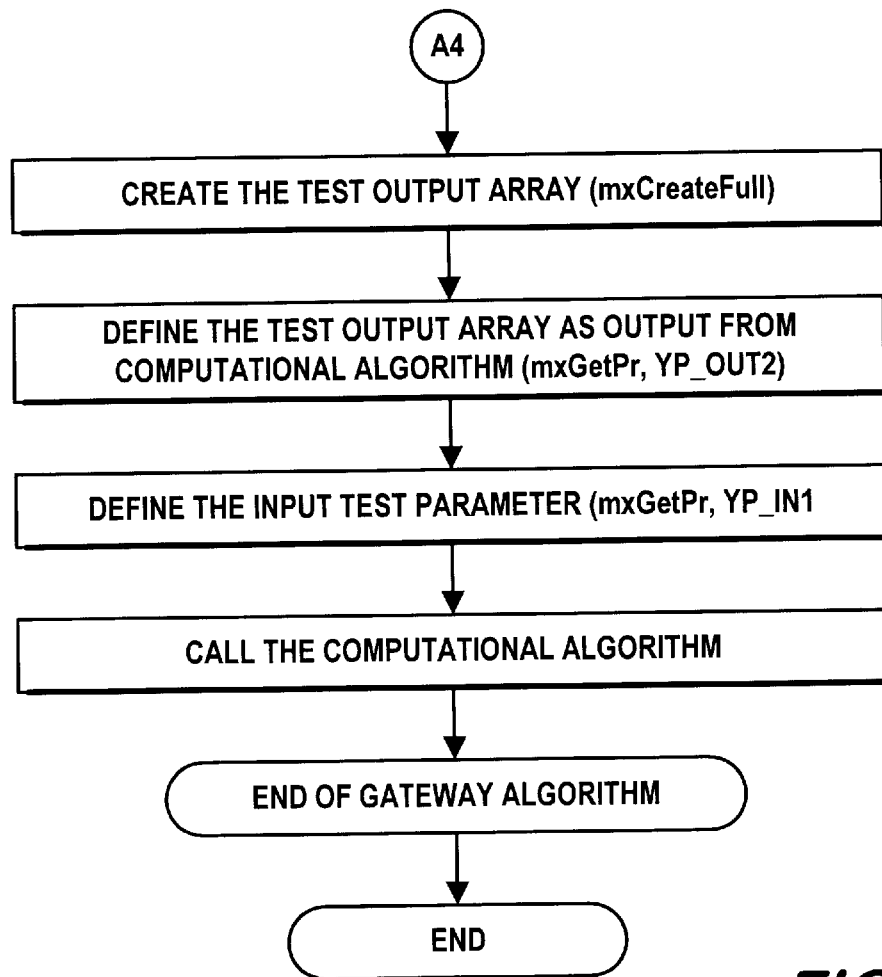

Turning now to FIG. 7, therein illustrated is a flow chart functionally setting forth the several steps in the method of the present invention. Initially, the computer is utilized to input the process parameters and constants and the boards and drivers are all initialize. A sampling can be taken of the signals being generated to ensure that the elements of the installation are operational.

In operation, the triggering event begins the dumping of processing of data through the DAS I/F board and the transfer of that data to the DAS Boards for processing in accordance with the present invention. Following such processing, the computer monitor displays the estimated fault location within the transformer being monitored.

The DAS I/F Board greatly improves efficiency and enables processing of eight times the signals and localizes the synchronized signals.

FIG. 8 is a listing of factors in the initialization sequence.

FIG. 9 is a flow chart illustrating the software utilized in the initialization of the apparatus to begin the processing of the signals.

Figure 10A:
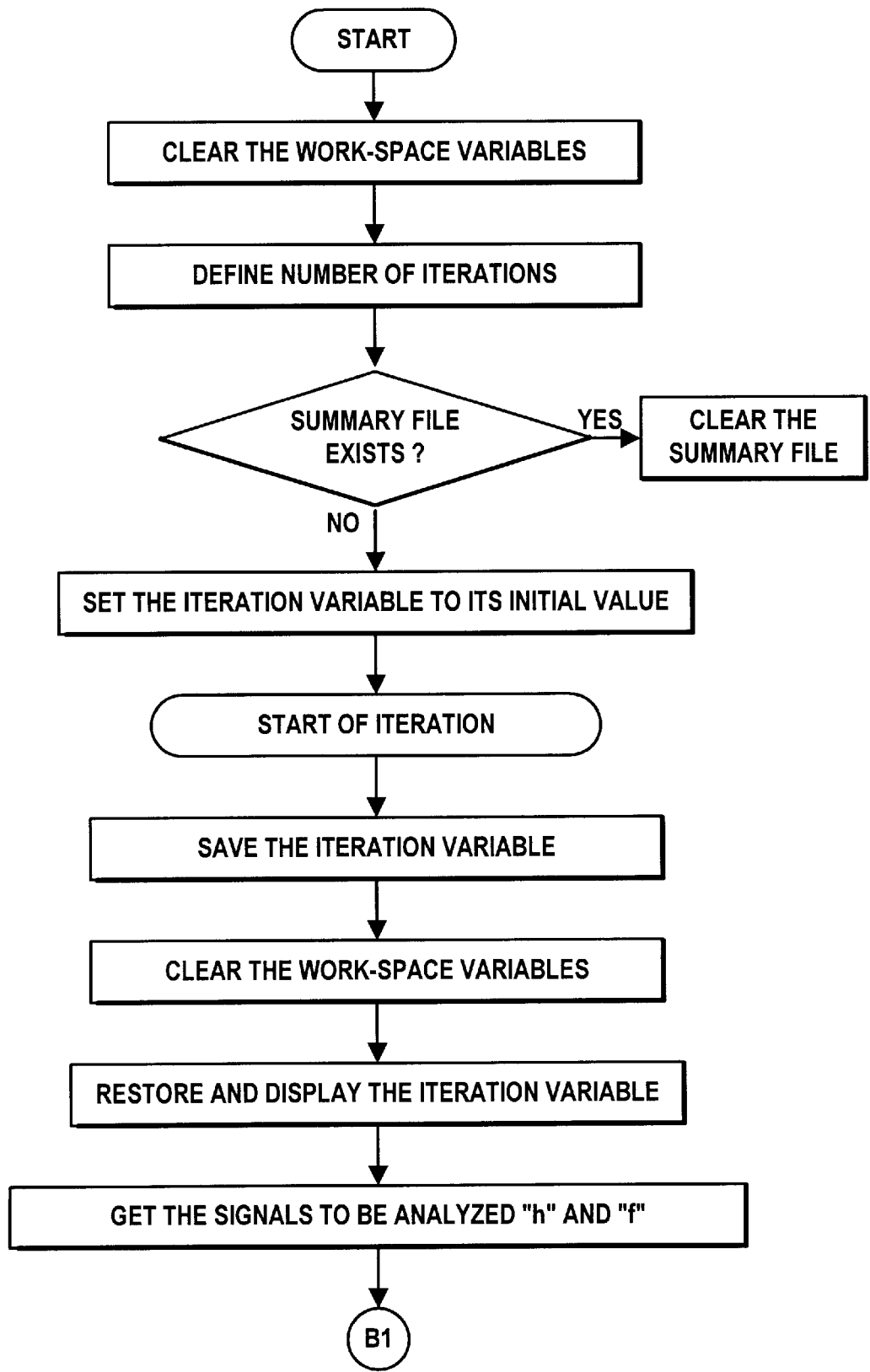
FIGS. 10a–10b comprise a flow chart of the software utilized for the wavelet processor initialization.
Figure 10B:
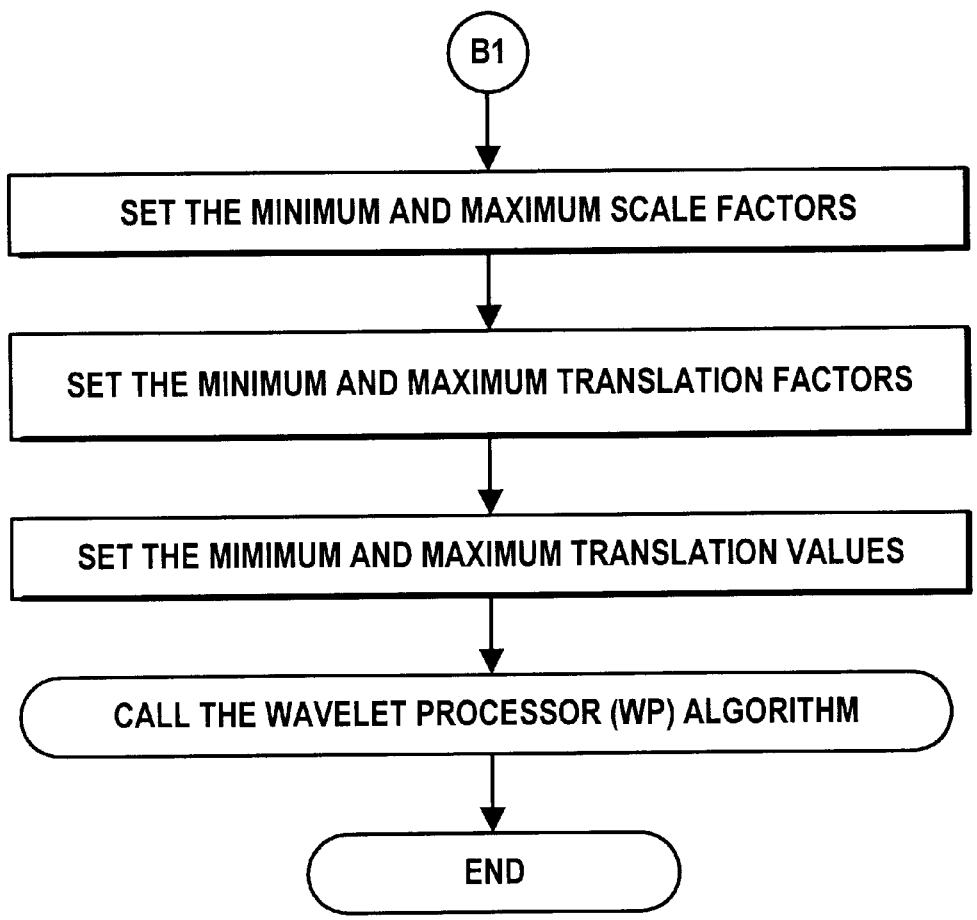
Figure 11A:
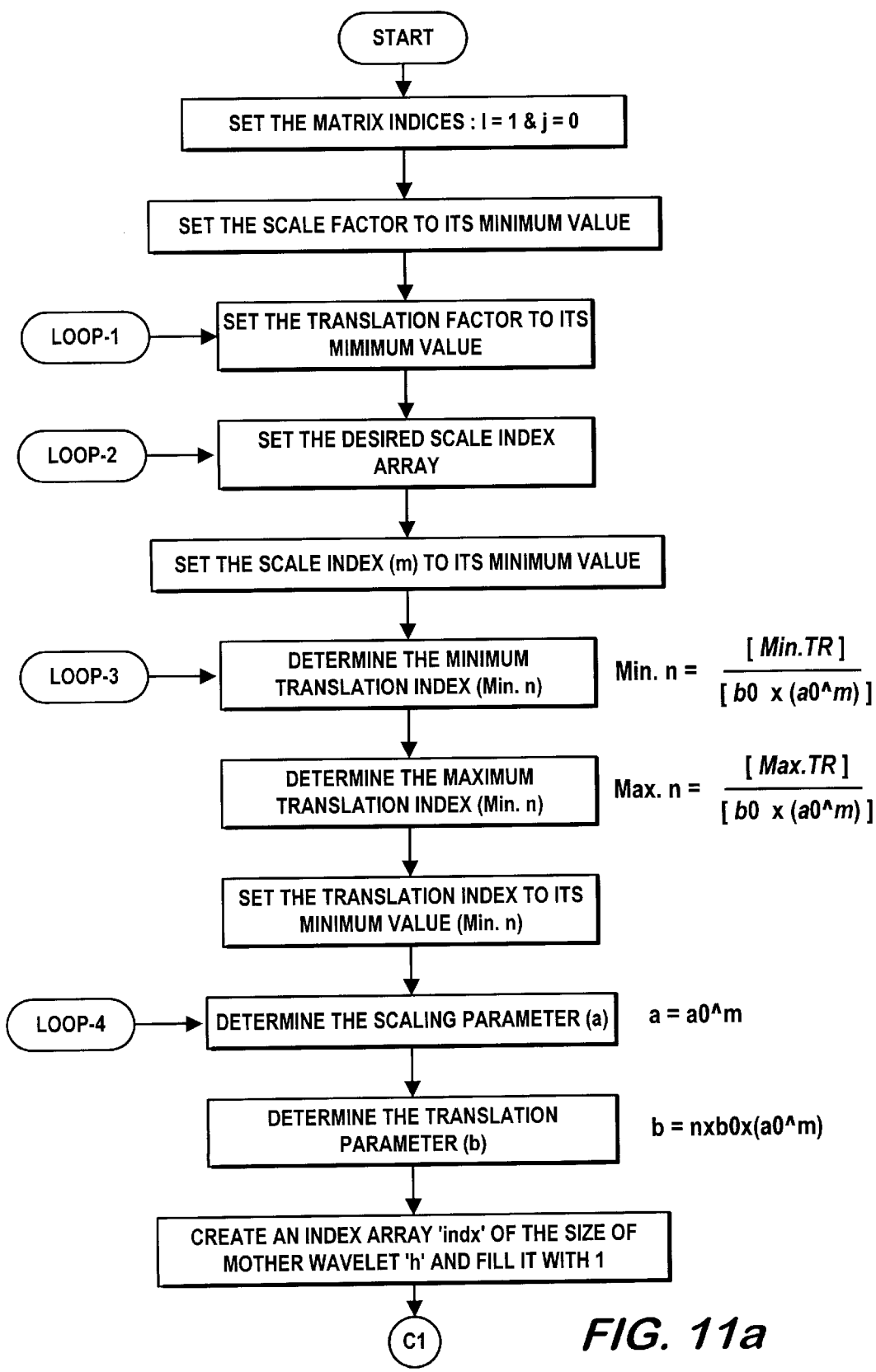
FIGS. 11a–11e comprise a flow chart of the software utilized for processing the wavelets to determine positional information.
Figure 11B:
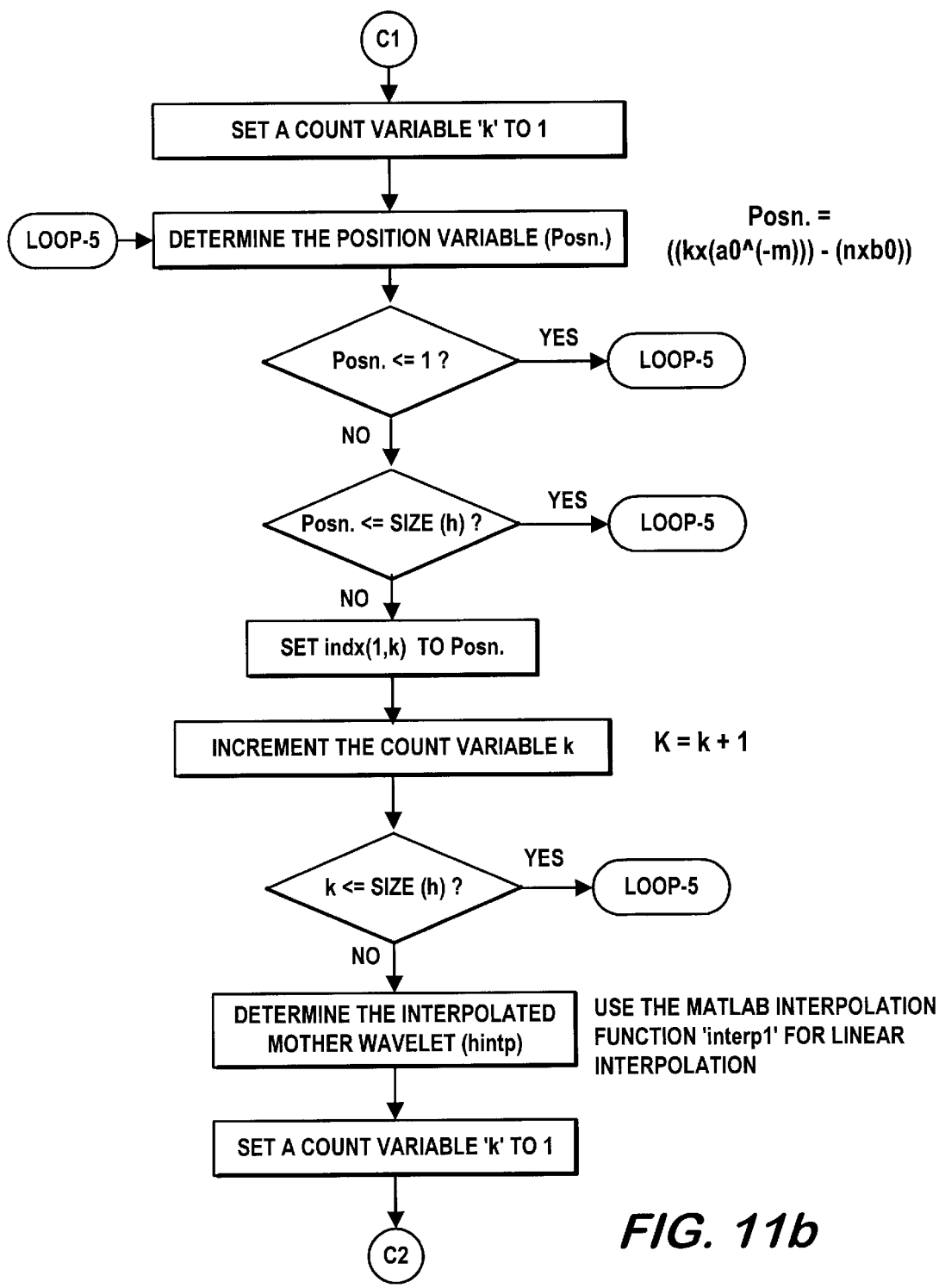
Figure 11C:
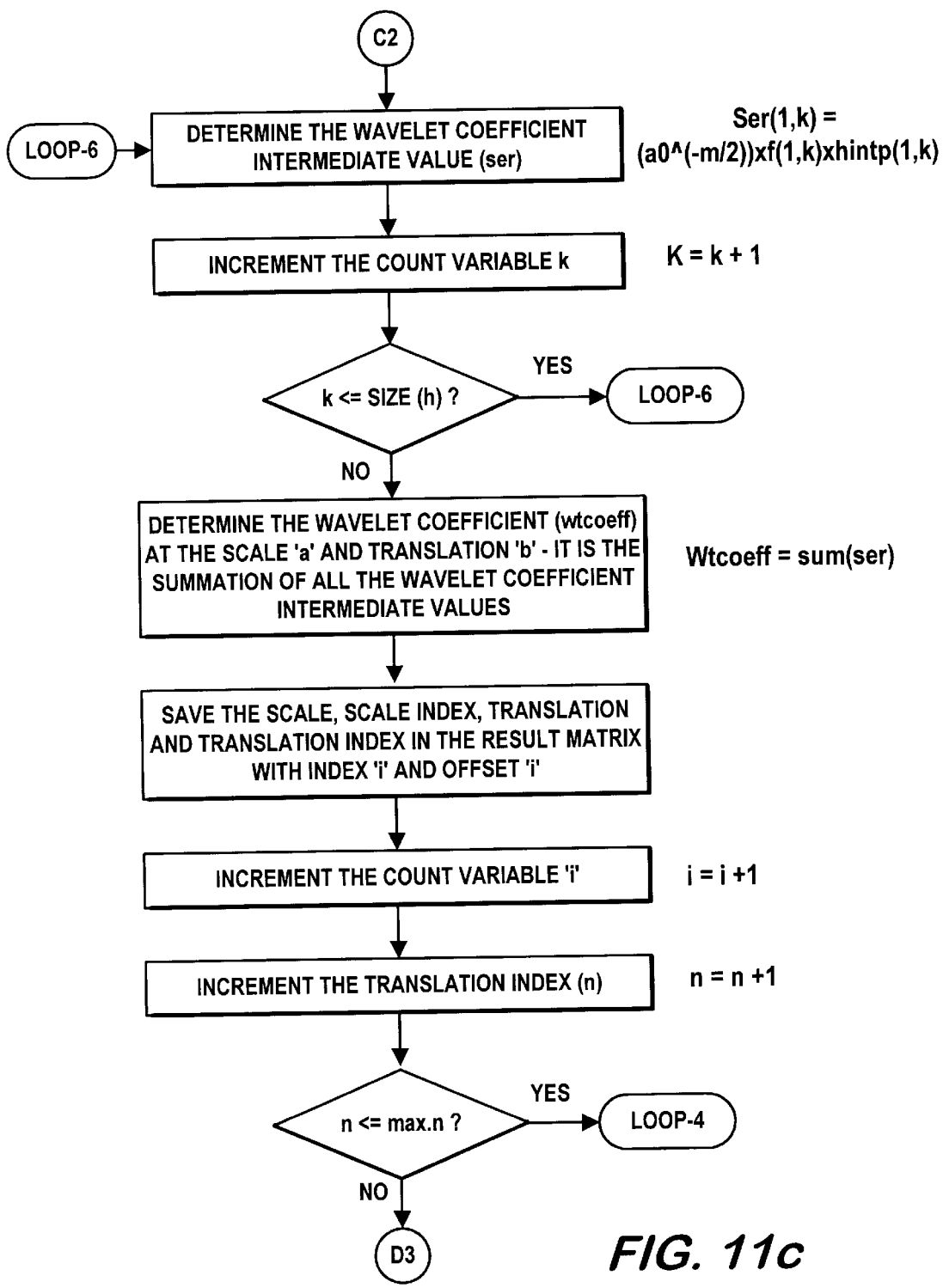
Figure 11D:
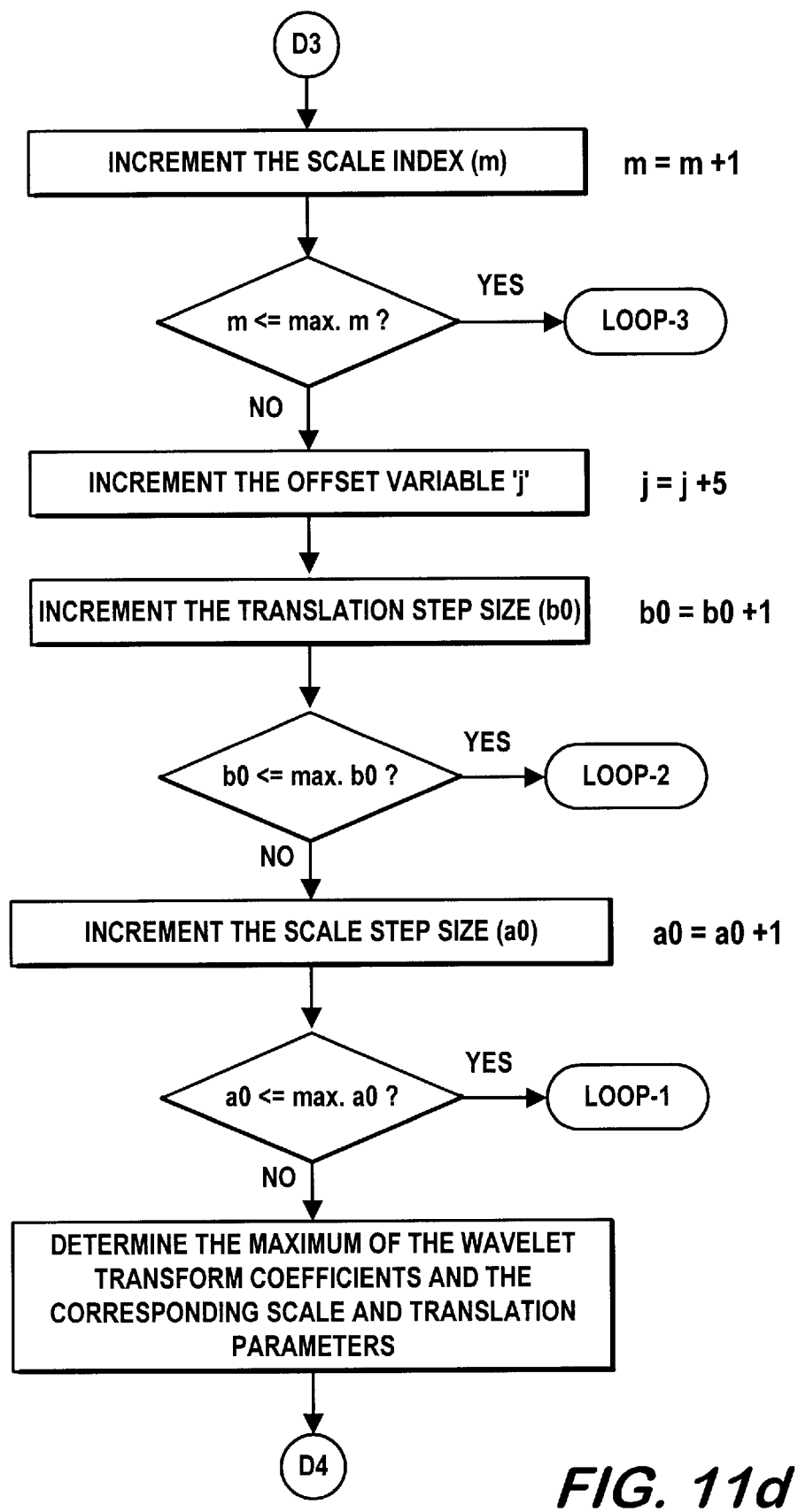
Figure 11E:
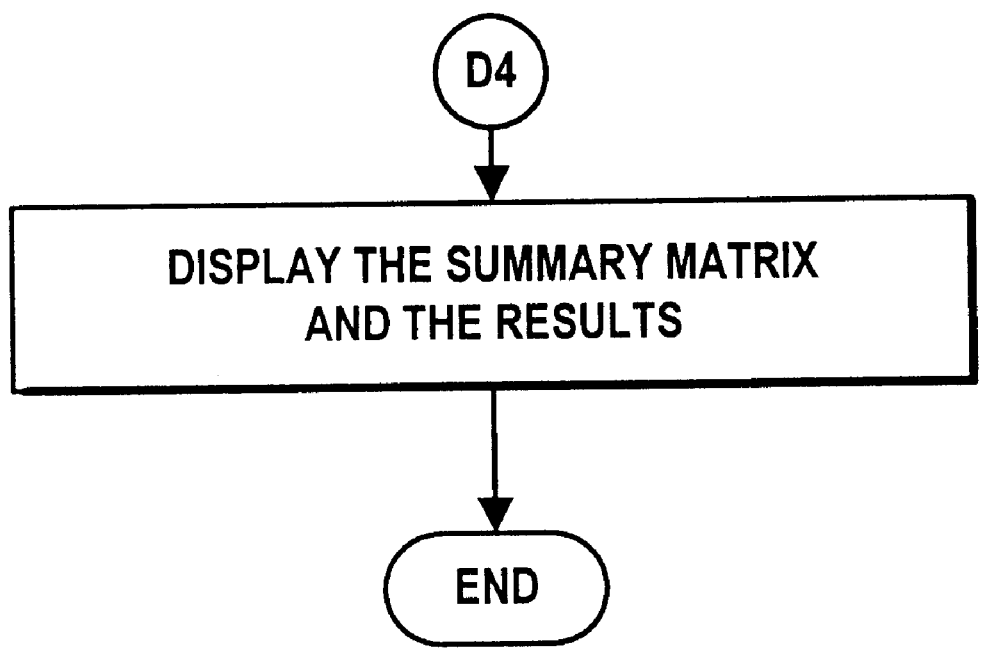

FIG. 10 is a flow chart of the software utilized for the wavelet processor initialization.

FIG. 11 is a flow chart of the software utilized for processing the wavelets to generate the positional information.

It will be appreciated that various modifications can be made in the several steps shown in the software so long as the basic principles enunciated previously are followed to ensure that there is adequate and appropriate correlation and localization of the triggering signal and the pulses from the various sensors. If so desired, the PC can be set up to run continuously and to indicate an alarm when a triggering signal is received.

Thus, it can be seen from the foregoing detailed description and attached drawings that the method of the present invention allows relatively accurate and facile determination of the approximation of the location of incipient faults in the insulation of a transformer. As a result, defects in the transformer insulation can be repaired before there is a catastrophic failure to reduce the possibilities of severe outages in a power distribution network or vast significant fluctuations in the power supply to various facilities being serviced. The apparatus for the practice of the method of the present invention can be readily fabricated from commercially available components and the software required for operation is relatively simple, easy to execute in accordance with the parameters hereinbefore set forth.

Having thus described the invention, what is claimed is:

1. In a method for determining the position of a partial discharge fault in a transformer tank, the steps comprising:

(a) securing supersonic sensors on a transformer tank at a multiplicity of points spaced about the periphery thereof;

(b) establishing a threshold amplitude and a frequency range for pulse vibrations to be evaluated;

(c) sensing supersonic vibrations at said multiplicity of points and transmitting signals from said sensors to an interface;

(d) multiplexing synchronizing and localizing at said interface said signals from said multiplicity of points and transmitting said multiplexed signals to a processor;

(e) processing said multiplexed signals by steps including:

(i) determining the existence of triggering pulse vibrations exceeding said established threshold amplitude and within said established frequency and range;

(ii) conducting a wavelet transform on the multiplexed signals from said sensors at said multiplicity of points two at a time with one signal being the signal from the first sensor found to provide a signal above said threshold amplitude, said wavelet transform providing both frequency and time domain;

(iii) applying a scaling factor and translation parameters associated with the frequency of said vibrations to obtain estimates of the time delays for triggering pulse vibrations detected at said multiplicity of points; and (iv) evaluating said estimates from the transformed and scaled signals to determine the position of the partial discharge fault generating said triggering pulse vibrations.

2. The method for determining the position of a partial discharge fault in a transformer tank in accordance with claim 1 wherein said processing step initially generates a triggering signal to said interface upon sensing a signal of greater amplitude than the predetermined value to initiate further processing steps.

3. The method for determining the position of a partial discharge fault in a transformer tank in accordance with claim 1 wherein said processing step includes passing said multiplexed signals into a data acquisition board which samples signals in several channels at a predetermined minimum sampling frequency per channel.

4. The method for determining the position of a partial discharge fault in a transformer tank in accordance with claim 3 wherein said sampling frequency is determined by the Nyquist Criterion.

5. The method for determining the position of a partial discharge fault in a transformer tank in accordance with claim 1 wherein there is included the step of timing the signals being processed in said multiplexing and processing steps.

6. Apparatus for determining the position of a partial discharge fault in a transformer tank comprising:

(a) a multiplicity of supersonic sensors for mounting on a transformer tank at a multiplicity of points spaced about the periphery thereof;

(b) an interface for receiving, multiplexing, synchronizing and localizing said signals from said multiplicity of sensors; and (c) a processor for said multiplexed signals including:

(i) means for determining the existence of triggering pulse vibrations exceeding an established threshold amplitude and within an established frequency and range;

(ii) means for conducting a wavelet transform on the multiplexed signals from said sensors at said multiplicity of points, two at a time with one signal being the signal from the first sensor found to provide a signal above said threshold amplitude, said wavelet transform providing both frequency and time domain;

(iii) means for applying a scaling factor and translation parameters associated with the frequency of said vibrations to obtain estimates of the time delays for triggering pulse vibrations detected by said multiplicity of sensors; and (iv) means for evaluating said estimates from the transformed and scaled signals to determine the position of the partial discharge fault generating said triggering pule vibrations.

7. The apparatus for determining the position of a partial discharge fault in a transformer tank in accordance with claim 6 wherein said interface produces synchronized multiplexed analog signals.

8. The apparatus for determining the position of a partial discharge fault in a transformer tank in accordance with claim 6 wherein said processor includes data acquisition boards which sample signals in several channels at a predetermined minimum sampling frequency per channel.

9. The apparatus for determining the position of a partial discharge fault in a transformer tank in accordance with claim 8 wherein said sampling frequency is determined by the Nyquist Criterion.

10. The apparatus for determining the position of a partial discharge fault in a transformer tank in accordance with claim 6 wherein there is included a clock circuit for timing the signals being processed in said interface and processor.

* * * * *